(12) United States Patent
Chakravarthy

(10) Patent No.: US 10,179,074 B2
(45) Date of Patent: Jan. 15, 2019

(54) ALGINATE WOUND DRESSING AND METHOD OF MAKING THE SAME

(75) Inventor: Debashish Chakravarthy, Vernon Hills, IL (US)

(73) Assignee: Medline Industries, Inc., Northfield, IL (US)

( * ) Notice: Subject to any disclaimer, the term of this patent is extended or adjusted under 35 U.S.C. 154(b) by 1350 days.

(21) Appl. No.: 13/549,839

(22) Filed: Jul. 16, 2012

(65) Prior Publication Data

US 2014/0018716 A1 Jan. 16, 2014

(51) Int. Cl.
| A61F 13/00 | (2006.01) |
| A61F 13/02 | (2006.01) |
| B29C 47/00 | (2006.01) |
| B29C 47/88 | (2006.01) |

(52) U.S. Cl.
CPC .. *A61F 13/00991* (2013.01); *A61F 13/00012* (2013.01); *A61F 13/00063* (2013.01); *A61F 13/0283* (2013.01); *B29C 47/0014* (2013.01); *B29C 47/8895* (2013.01); *A61F 2013/0091* (2013.01); *A61F 2013/00229* (2013.01); *A61F 2013/00744* (2013.01); *A61F 2013/00748* (2013.01); *A61F 2013/00936* (2013.01); *B29C 47/0064* (2013.01)

(58) Field of Classification Search
None
See application file for complete search history.

(56) References Cited

U.S. PATENT DOCUMENTS

| 5,690,955 | A | 11/1997 | Griffiths et al. |
| 5,714,232 | A | 2/1998 | Fenton et al. |
| 6,080,420 | A | 6/2000 | Qin et al. |
| 6,114,594 | A | 9/2000 | Barikosky |
| 6,458,460 | B1 | 10/2002 | Griffiths et al. |
| 6,638,881 | B2 | 10/2003 | Lapidus |
| 6,656,974 | B1 | 12/2003 | Renn et al. |
| 7,229,689 | B2 * | 6/2007 | Qin et al. ............ 428/372 |
| 2009/0287130 | A1 | 11/2009 | Lee et al. |
| 2010/0260824 | A1 * | 10/2010 | Shah ............ A01N 25/00 424/447 |
| 2011/0021964 | A1 * | 1/2011 | Larsen et al. ............ 602/47 |
| 2011/0027344 | A1 | 2/2011 | Lee et al. |
| 2012/0009241 | A1 | 1/2012 | Yang |

OTHER PUBLICATIONS

Kim, Seung B., "International Search Report and Written Opinion", PCT/US2013/049588; Filed Jul. 8, 2013; dated Oct. 15, 2013.

\* cited by examiner

*Primary Examiner* — Ophelia A. Hawthorne
*Assistant Examiner* — Caitlin Carreiro
(74) *Attorney, Agent, or Firm* — Philip H. Burrus, IV

(57) ABSTRACT

A method (400) of manufacturing a wound dressing includes obtaining alginate fibers (108) and the step (404) of spraying either the alginate fibers (108) or a dressing or dressing layer (610) of the alginate fibers with an aqueous solution (801) comprising a polysaccharide, which can be carboxymethylcellulose. The step of spraying can occur while the alginate fibers, dressing, or dressing layer are wet. A step (405) of flash drying can follow to remove the solute of the aqueous solution to leave the polysaccharide along the alginate. The step of spraying can be selective, such that only portions of the dressing layer include the polysaccharide.

13 Claims, 12 Drawing Sheets

ALGINATE WOUND DRESSING AND METHOD OF MAKING THE SAME

BACKGROUND

Technical Field

This invention relates generally to a wound dressing, and more particularly to an alginate wound dressing.

Background Art

Alginate fibers are known to be of value in healing wounds. It is generally understood that wounds are to be kept generally dry to facilitate healing. The use of gauze, which is a cotton based product, while helpful, is not optimal for healing wounds due to its tendency to adhere to tissue about the wound when liquids are exuded. Alginates are a useful substitute for gauze due to their ability to absorb liquids in a less adherent manner than gauze dressings.

Alginates are a polymer product that may be obtained from algae and other similar organisms. Many alginates employed in wound dressings are derived from seaweed. Specifically, a solution comprising a soluble alginate polymer made from various mannuronic and gulurnic residues of the seaweed. The solution is then extruded into a bath where an insoluble form of the alginate precipitates. This alginate can then be spun to form fibers used in wound dressings. While prior art alginate dressings adequately well in practice, they do not fully eliminate the adherent issue discussed above. It would be advantageous to have an improved alginate dressing that reduced the likelihood that the dressing would adhere to a wound, while at the same time being simple and inexpensive to manufacture.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
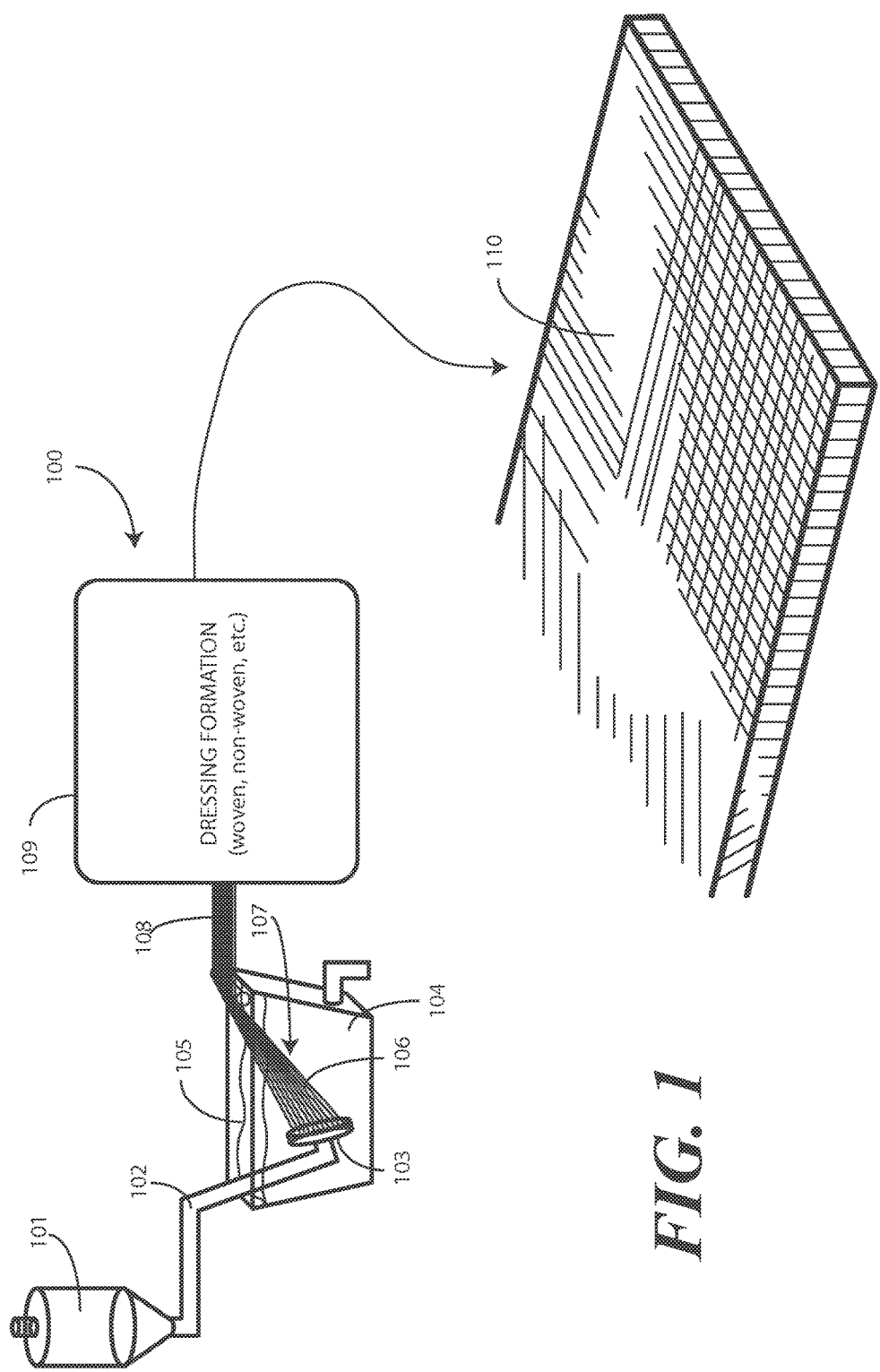
FIG. 1 illustrates one method of forming an alginate dressing in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

In the manufacture of prior art alginate dressings, alginate fibers are often extruded into, and spun out of, a bath containing a solution of calcium chloride. The introduction of a soluble form of an alginate polymer into such a bath results in a precipitation of insoluble calcium alginate. The fibers can then be woven into a dressing. Fibers manufactured in this fashion tend to have an increased absorbency when compared to other materials, such as the cotton fibers used in gauze dressings. The calcium alginate functions to absorb liquids exuded from wounds.

There have been attempts to improve the wettability and gelling nature of the alginate fibers. For example, some have attempted to incorporate polysaccharide fibers into the alginate fibers through either a blending process that occurs at a pre-extrusion stage, or through a co-spinning process. U.S. Pat. No. 6,458,460 to Griffiths et al., which is incorporated herein by reference, describes the former, while U.S. Pat. No. 6,080,420 to Qin et al. describes the latter. In both cases, the polysaccharide used is carboxymethylcellulose.

There are significant problems with these attempts to incorporate carboxymethylcellulose into alginate fibers. Illustrating first with the blending process, this process requires that soluble carboxymethylcellulose and soluble alginate must be mixed prior to extruding the material into the calcium chloride bath. While this process is viable, it is generally cost prohibitive. While some customers of a manufacturer may desire an alginate/polysaccharide blend, most do not. Consequently, strict compliance with very particular processes to clean out mixing tanks and bath facilities is required to produce pure alginate fibers in subsequent runs. Compliance with these processes is very costly.

With the co-spinning process, carboxymethylcellulose fibers are co-spun with alginate fibers. The problems with this process are that carboxymethylcellulose fibers are manufactured with the use of harsh reagents that have harmful environmental consequences. Consequently, only a couple of manufacturers of carboxymethylcellulose fibers exist. It is therefore difficult for one desiring to practice the co-spinning process to obtain the carboxymethylcellulose fibers required for the process.

Embodiments of the present invention eliminate both issues. In accordance with one or more embodiments of the invention, polysaccharides such as carboxymethylcellulose are more easily incorporated into alginate fibers. While carboxymethylcellulose is one example of such a polysaccharide, embodiments of the present invention are applicable for any polysaccharide that is soluble in a solvent or suspendable in a suspending agent. In one embodiment, carboxymethylcellulose is soluble in water. Alginate fibers, post-spinning but still moist from the extrusion bath, are sprayed with the solution of carboxymethylcellulose in water to incorporate the carboxymethylcellulose into the alginate fibers. In other embodiments, the spraying step can occur after the needling stage (where applicable) or after the lapping stage (where applicable). The spraying step can be performed in many different locations between the alginate precipitation stage and the final rolling stage of materials comprising the alginate fibers.

After the spraying process is applied, the solvent can be flashed out with a drying process. For example, if the spray comprises carboxymethylcellulose suspended in water, after the spraying step the water can be flashed during a drying step to leave only a contact layer of carboxymethylcellulose along the alginate fibers or, where the spraying was done post needling, particles of carboxymethylcellulose disposed along the alginate fibers.

While greatly simplifying and reducing cost from the manufacturing process, embodiments of the invention have other advantages as well. The fact that the polysaccharide solution is sprayed onto the wet alginate fibers allows for the selective deposition of that polysaccharide along any resulting dressing. While the inclusion of the polysaccharide increases the absorption of the resulting dressing and decreases the probability that the dressing will stick to a tissue or would exudate, it is contemplated that there are a variety of reasons why one would not want the polysaccharide to be applied to the entire dressing. In one embodiment, for example, the medication can be integrated into the alginate fibers. Silver ions or other medication can be applied to or integrated into the alginate fibers for selective release into a wound. The omission of a polysaccharide in locations where medication was used would work to increase the facilitation of the transport of the medication to the wound. At the same time, the inclusion of the polysaccharide in other locations would increase the absorbency and reduce the tendency to adhere without impeding the medicinal transport. The selective deposition can be performed in a repeating, periodic pattern, such as in a linear pattern, dotted pattern, or other similar pattern. Alternatively, the deposition can be in accordance with a non-periodic pattern designed for a specific application. The prior art co-blending and co-spinning does not allow for the creation of selective arrangements where a dressing has some portions defined by alginate and the polysaccharide, while other portions are alginate only.

In one embodiment of the invention, a method of manufacturing a wound dressing includes extruding alginate to form one or more alginate fibers. In one embodiment, the alginate is extruded into a bath, which can be a calcium chloride bath. While the fibers are still wet from the extrusion bath, the fibers are sprayed with a solution comprising a polysaccharide. In one embodiment, the solvent of the solution is water and the polysaccharide is carboxymethylcellulose. In one embodiment, the spraying step comprises spraying an amount of the solution sufficient to apply an amount of the carboxymethylcellulose that is about fifteen percent by weight of the one or more alginate fibers.

The fibers are then formed into a dressing. In one embodiment, this involves weaving the fibers into a woven pattern. In another embodiment, this involves manufacturing a nonwoven material layer. The spraying step can occur before the fibers are formed into the dressing, or after. In one embodiment, the spraying step is done selectively so that some portions of the resulting dressing include the polysaccharide while other portions of the resulting dressing do not include the polysaccharide. The fibers and/or dressing can be exposed to a drying step to flash away the solvent to leave only the solute of the spraying step upon the alginate fibers.

Medication, such as silver ions, can be applied to the alginate fibers and/or dressing as well. In one embodiment where the polysaccharide is selectively deposited, the medication is applied only to portions not containing the polysaccharide.

The resulting wound dressing thus comprises a dressing layer manufactured from alginate fibers and either a layer of polysaccharide or particles of the polysaccharide deposited thereon. In one embodiment, the layer of polysaccharide or particles of polysaccharide are selectively deposited along the dressing. Examples of selective deposition include repeating patterns, periodic patterns, non-repeating patterns, non-periodic patterns, symmetric patterns, asymmetric patterns, and free-form patterns. The selective deposition can occur only at a wound-covering location, or at the complement of this location, the latter being more applicable when medicine is applied to the dressing at the wound-covering location.

Turning now to FIG. 1, illustrated therein is a schematic block diagram of an alginate dressing manufacturing operation 100 suitable for use with embodiments of the invention. A mixing tank 101 holds a soluble form of a polymer, which in one embodiment is a soluble form of an alginate. The soluble alginate is fed through a tube to a spinneret head 103 disposed within a bath 104. The bath 104 contains a solution 105. In one embodiment, the solution 105 is a calcium chloride solution.

When extruded from the spinneret head 103, the soluble alginate precipitates into one or more alginate fibers 106.

Where the solution 105 is calcium chloride, the one or more alginate fibers 106 comprise insoluble calcium alginate. The one or more fibers 106 are then spun 107 into fibers 108 that can be used in a dressing formation process 109 that is used to manufacture a dressing 110 from the fibers 108. A vertically integrated manufacturer could employ the operation 100 of FIG. 1 to manufacture the dressing 110. A less vertically integrated manufacturer may instead perform the step of obtaining alginate fibers (rather than manufacturing them) and then forming them into a dressing material.

Figure 2:
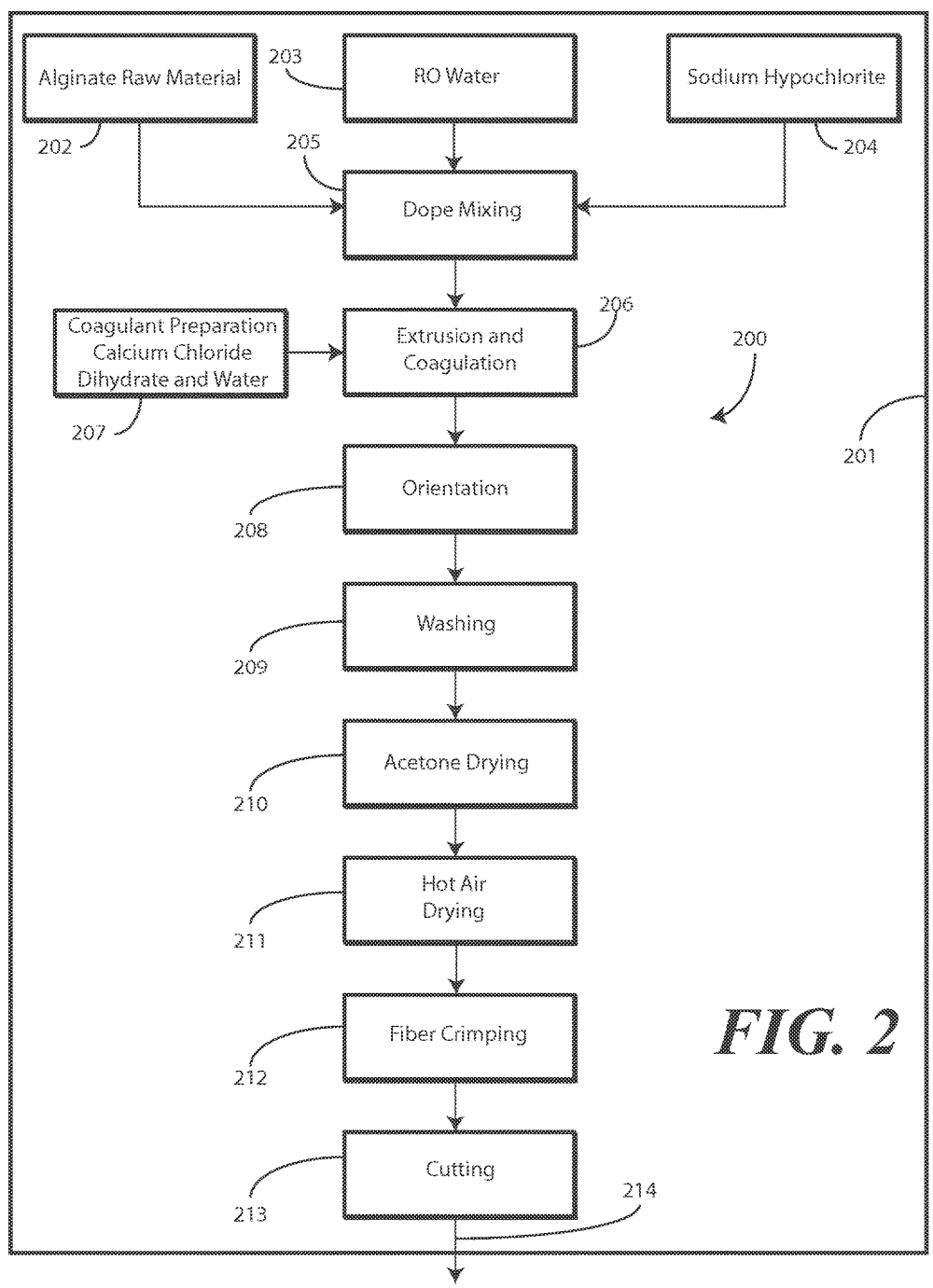
FIG. 2 illustrates one explanatory method of forming alginate fibers in accordance with one or more embodiments of the invention.

Turning now to FIG. 2, illustrated therein is a method 200 for forming alginate fibers that can be used in an alginate dressing manufacturing operation (100) configured in accordance with one or more embodiments of the invention. The steps of FIG. 2 preferably take place in a clean room 201, which in one embodiment is a class 10,000 clean room.

The raw materials to be placed in the mixing tank (101) include alginate powder 202, water 203, and sodium hypochlorite 204. These raw materials are mixed to form a "dope" 205 that is placed within the mixing tank (101). The solution (105) for the bath (104) is prepared at step 207. In this illustrative embodiment, the solution (105) comprises calcium chloride dihydrate mixed with water.

At step 206, the dope 205 is extruded through the spinneret head (103). The strands of dope material then coagulate and precipitate into one or more alginate fibers (106). The one or more alginate fibers (106) are then oriented at step 208. The orienting step 208 can be performed by rotation or other animation of the spinneret head (103). Alternatively, the orienting step 208 can be performed as a portion of the extraction process that occurs when the one or more alginate fibers (106) are pulled from the bath (104).

At step 209, the one or more alginate fibers (106) are washed. At step 210, acetone is removed from the one or more alginate fibers (106). At step 211, the one or more alginate fibers (106) are dried. In one embodiment, step 211 comprises flash drying the one or more alginate fibers with heat to remove the water.

At optional step 212, the resulting fibers can be crimped or otherwise formed for processing. Once suitably formed, if desired, the resulting fibers can be cut to length at step 213. The resulting fibers then exit 214 the clean room 201 for further processing, such as for forming into a dressing (110).

Figure 3:
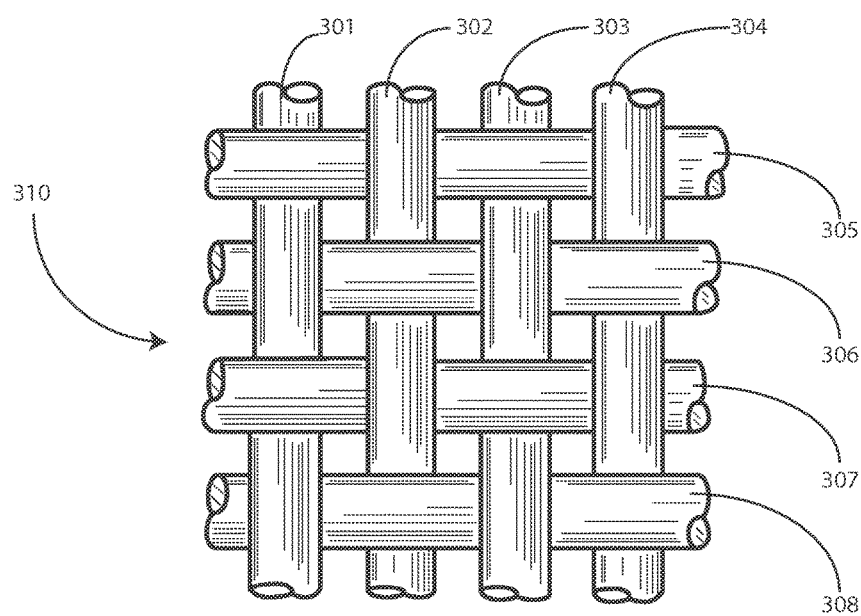
FIG. 3 illustrates one explanatory woven alginate dressing configured in accordance with one or more embodiments of the invention.
Figure 4:
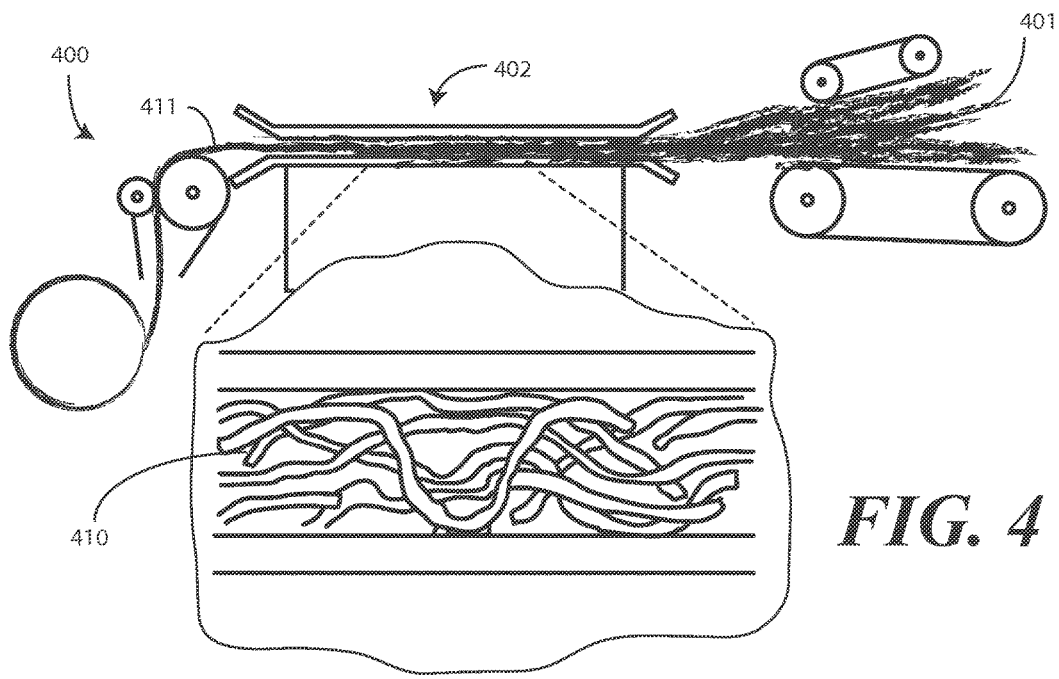
FIG. 4 illustrates one explanatory method of manufacturing a non-woven alginate dressing configured in accordance with one or more embodiments of the invention.

Note that the dressing 110 can be formed in a variety of ways. For example, turning now to FIG. 3, illustrated therein is a dressing material 310 that is woven. Alginate fibers 301,302,303,304 can be extended in a first direction while other alginate fibers 305,306,307,308 can be woven therebetween to form a woven layer. Turning to FIG. 4, illustrated therein is an method 400 for manufacturing a dressing material 410 that is non-woven.

As shown in FIG. 4, a non-woven bunch of fibers 401 are fed into a forming machine 402 where they are interlocked without weaving. For example, in one embodiment felting needles (not shown) can pass through the non-woven bunch of fibers 401 to perform the interlocking step to form the non-woven dressing material 410. In other embodiments, non-woven bunch of fibers 401 can be formed from a spunbond or carded web. The resulting layer 411 of dressing material 410 can be spooled for later processing.

Figure 5:
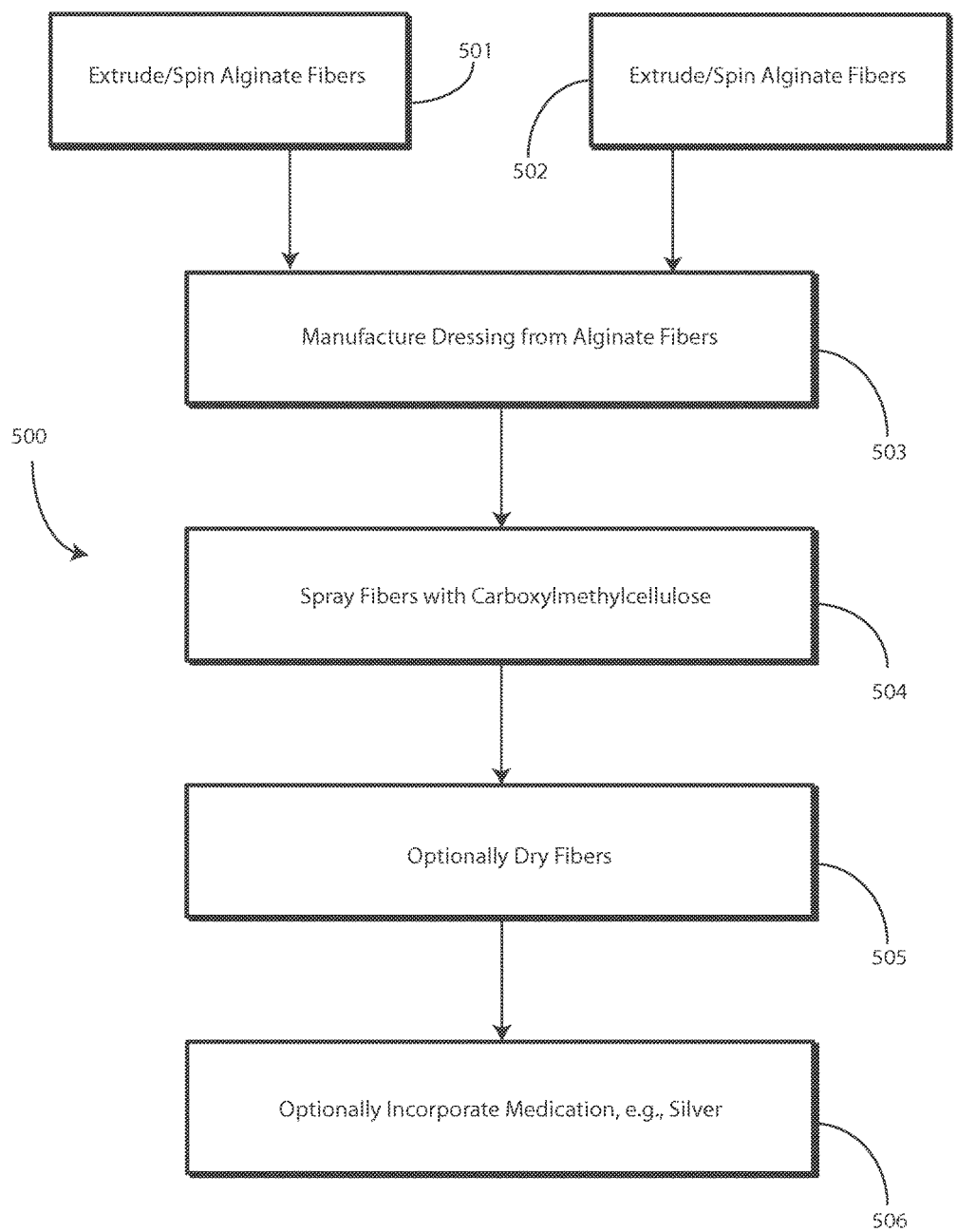
FIG. 5 illustrates one explanatory method of manufacturing a dressing in accordance with one or more embodiments of the invention.

Turning now to FIG. 5, illustrated therein is one explanatory method 500 of manufacturing a wound dressing in accordance embodiments of the invention that integrate a polysaccharide, such as carboxymethylcellulose, into the dressing itself. At step 501, in one embodiment, alginate is extruded to form one or more alginate fibers. The operation (100) of FIG. 1, or another operation that may be readily apparent to those of ordinary skill in the art having the benefit of this disclosure, can be used to extrude the alginate fibers in this step 501. In one embodiment, step 501 can include extruding the one or more alginate fibers into a bath. In one embodiment, the bath can comprise a solution of calcium chloride.

In one embodiment, step 501 can include a spinning step to spin the one or more fibers into a fiber suitable for weaving into a dressing layer or, alternatively, that is suitable for forming a non-woven dressing layer. For example, a spinneret head can be rotated in the bath while the alginate is extruded. Alternatively, the one or more fibers in the bath may be gathered and spun as they are extracted from the bath. In yet another embodiment, the one or more fibers are extracted and are then spun in a post-bath process.

For those manufacturing dressings in accordance with embodiments of the invention who do not have access to alginate fiber manufacturing operations, step 502 can be substituted for step 501. At step 502, a dressing manufacture simply obtains alginate fibers from an alginate fiber manufacturer. In one embodiment, these fibers are obtained while wet. Optionally, step 502 can comprise obtaining a dressing material from an alginate fiber manufacturer, e.g., where the alginate manufacturer both manufactures the one or more fibers and also includes an equivalent of the dressing formation process (109) shown in FIG. 1. In one embodiment, this procurement of the dressing material comprises procuring the dressing material before the fibers therein are completely dried of the solution in which they were precipitated.

At step 503, the alginate fibers are formed into a dressing or a dressing material. As set forth above in FIGS. 3 and 4, in one embodiment the dressing or dressing material output from step 503 is woven. In another embodiment, the dressing or dressing material is non-woven.

At step 504, either the one or more fibers from step 501 or the dressing or dressing material of step 503 are sprayed with a solution comprising a polysaccharide. As noted above, in one embodiment the polysaccharide comprises carboxymethylcellulose. Since the spraying of step 504 can be applied to either the one or more fibers of step 501 or the dressing or dressing material of step 503, it is noted that step 504 can come before or after step 503. This will be described in more detail with reference to FIGS. 6-13 below.

In one embodiment, the spraying of step 504 occurs when the one or more fibers from step 501 or the dressing or dressing material of step 503 is wet. For example, in one embodiment, the one or more fibers are pulled from the bath used at step 501 and are sprayed with the solution comprising the carboxymethylcellulose or other polysaccharide occurs prior to the bath precipitant being completely dried away from the one or more fibers, i.e., while the one or more fibers are still wet from the bath, to help facilitate bonding between the polysaccharide and the one or more fibers. Where the spraying of step 504 occurs after the forming of the dressing or dressing material at step 503, this can also occur while the one or more fibers are still wet from the bath. Alternatively, the dressing or dressing material may be rewet to facilitate bonding.

In one embodiment, step 504 comprises spraying an amount of the polysaccharide along the one or more fibers and/or the dressing or dressing layer so as to provide a predetermined amount of the polysaccharide on the alginate per unit weight. For example, in one embodiment step 504 comprises spraying an amount of the solution sufficient to apply an amount of the carboxymethylcellulose that is about fifteen percent by weight of the one or more alginate fibers. In one embodiment, this can be achieved by spraying a solution comprising carboxymethylcellulose in water at a concentration of about ten percent.

In one embodiment, step 504 comprises selectively spraying the solution comprising the polysaccharide along the one or more fibers or the dressing or dressing material. Selectively spraying or selectively depositing means that some portions of the material are sprayed, while others are not sprayed. Said differently, the spraying step 504 can comprise "selectively" spraying such that the polysaccharide is applied to only select portions of the dressing. As will be described with reference to FIGS. 15-18 below, selectively depositing the polysaccharide can lead to numerous advantages that are not possible with prior art methods. The selective spraying can result in repeating patterns, periodic patterns, non-repeating patterns, non-periodic patterns, symmetric patterns, asymmetric patterns, and free-form patterns. For example, in one embodiment where step 504 occurs after step 503, step 504 comprises depositing the polysaccharide a repeating pattern along a dressing layer. In another embodiment where step 504 occurs after step 503, step 504 can comprise depositing the polysaccharide only on a wound-covering subportion of a dressing layer. The opposite can also be true, as in another embodiment step 504 comprises depositing the polysaccharide only on portions of a dressing layer that are complements of the wound-covering subportion.

At step 505, the method 500 can optionally include the step of drying the one or more fibers or the dressing or dressing material. In one embodiment, step 505 comes after the spraying step 504. In one embodiment step 505 comprises a flash drying process in which the one or more fibers or the dressing or dressing material is flash dried to remove all solution used in the spraying step 504. This leaves either a contact layer or internal particles of the polysaccharide. For example, where both the spraying step 504 and the optional drying step 505 occur prior to the forming step 503, a contact layer of the polysaccharide will remain along the one or more fibers. Where the spraying step 504 and the optional drying step 505 occur after the forming step 503, particles of the polysaccharide will remain on the dressing or dressing material.

In one or more embodiments, medication or other materials suitable for use in wound dressings can be applied to the one or more fibers or the dressing material or dressing at optional step 506. For example, in one embodiment silver ions can be integrated into the alginate fibers due to their medicinal effect. An example of how this can be accomplished is set forth in U.S. Pat. No. 7,229,689 to Qin et al., which is incorporated herein by reference. In one embodiment, where medicine or other materials are incorporated into the dressing, these materials can be selectively deposited. Further, in one or more embodiments, spraying step 504 can comprise not spraying the polysaccharide in locations where the medicine or other materials are intended to be delivered from the dressing to the patient.

Figure 6:
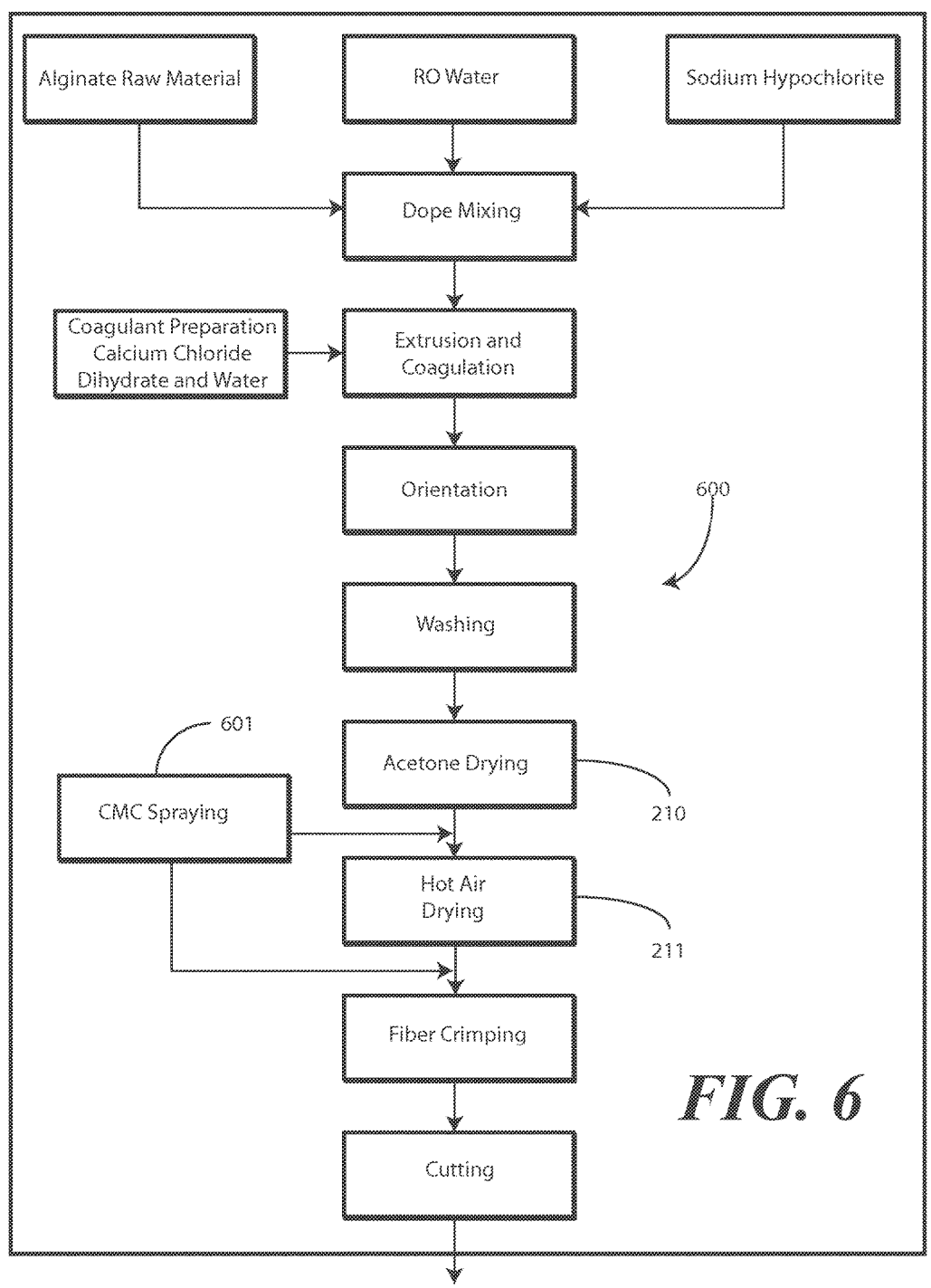
FIG. 6 illustrates one explanatory method of manufacturing alginate fibers comprising carboxymehtylcellulose in accordance with one or more embodiments of the invention.
Figure 7:
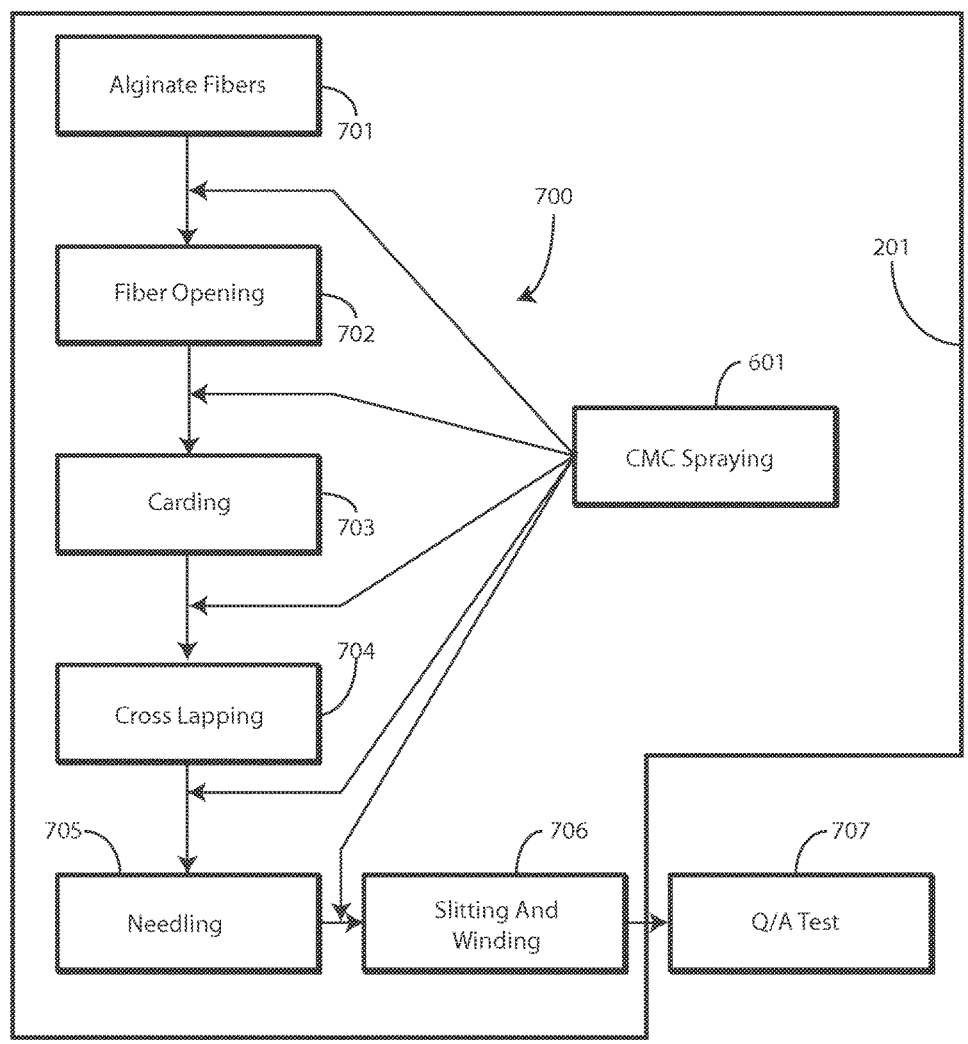
FIG. 7 illustrates one explanatory method of forming an alginate dressing comprising carboxymethylcellulose in accordance with one or more embodiments of the invention.

With the general steps of FIG. 5 in mind, and in particular the spraying step 504, FIGS. 6 and 7 illustrated various methods 600,700 of manufacturing alginate fibers comprising carboxymethylcellulose in accordance with one or more embodiments of the invention. FIG. 6 illustrates a method 600 that includes extruding the fibers themselves, while FIG. 7 illustrates a method of incorporating the carboxymethylcellulose into pre-made fibers. The former method 600 is more suitable for the vertically integrated manufactured noted above, while the latter method 700 is more suited for a more horizontally integrated manufacturer.

Turning to FIG. 6, illustrated therein is substantially the method (200) of FIG. 2. However, the method 600 of FIG. 6 includes the spraying step (504) from FIG. 5 that is used to deposit carboxymethylcellulose onto the one or more fibers (106) that are extruded from the bath (104). As shown in FIG. 6, the spraying 601 of the carboxymethylcellulose can occur after the step 210 of removing the acetone from the one or more fibers (106) or after the step 211 of flash drying the one or more fibers (106). In the former location, the one or more fibers (106) will still be wet from the bath (104). In the latter location, the one or more fibers (106) will be dry. FIG. 6 illustrates the flexibility of carboxymethylcellulose application contemplated by embodiments of the present invention.

Turning now to FIG. 7, in this method 700, alginate fibers 701 are premanufactured and are brought into a clean room 201. The fibers are opened 702 in the clean room 201 and are carded at a carding step 703 in accordance with carding processes known in the art. At step 704, the alginate fibers 701 can be cross lapped. In one embodiment, the cross lapping step 704 results in the dressing material (310) of FIG. 3. This dressing material (310) can then be needled at step 705 to obtain the proper dressing properties desired in the final product. Slitting and winding can occur at step 706. The resulting product then leaves the clean room and is optionally passed to a quality assurance group 707 for final testing.

Figure 8:
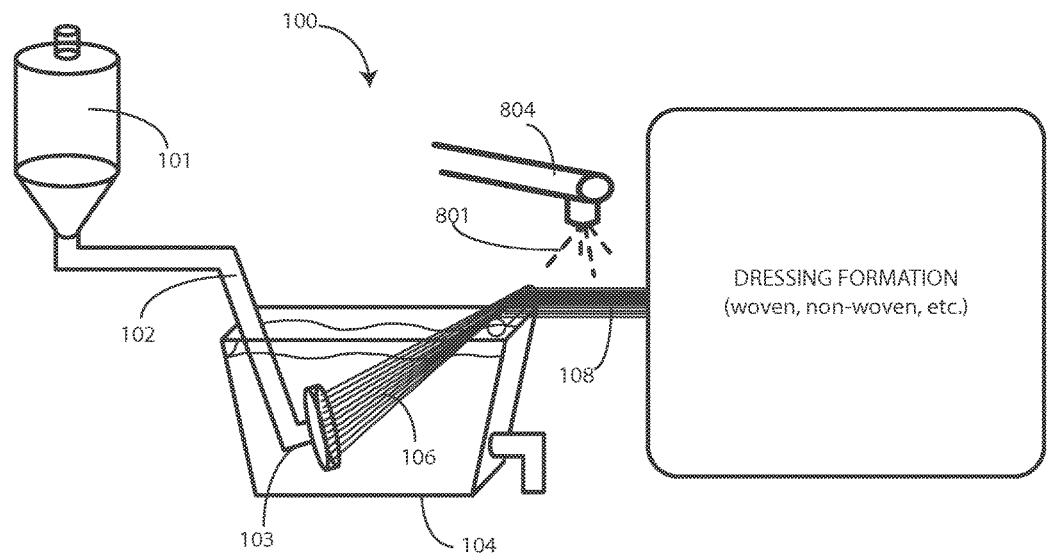
FIG. 8 illustrates one explanatory method of manufacturing alginate fibers comprising carboxymethylcellulose in accordance with one or more embodiments of the invention.

Turning now to FIGS. 8-13, illustrated therein are various points in respective dressing forming operations where a polysaccharide can be applied to alginate fibers. Beginning with FIG. 8, illustrated therein is the operation 100 of FIG. 1 with the inclusion of an additional spraying step 804. As the fibers 108 are drawn from the bath 104, but while still being wet from the bath 104, a spray of an aqueous solution 801 delivers a polysaccharide, such as carboxymethylcellulose is applied to the fibers 108. The aqueous solution can be formed from alginate powder that is dissolved in a solute or suspended in a suspension agent. It is contemplated that this process is far easier than the co-spinning prior art process described above because alginate powder does not require the harsh reagents used in the manufacture of carboxymethylcellulose fibers. Consequently, alginate powder does not have the environmental issues associated with the fibers. Further, alginate powder is available from a variety of manufacturers at a relatively low cost. An added benefit to the operation of FIG. 8 is that there need not be special, costly, and complex cleanout processes for any of the mixing tank 101, the feed tube 102, the spinneret head 103, or the bath 104 due to the fact that the polysaccharide is applied to the fibers 108 post-bath. The operation 100 of FIG. 8 is illustrative of a portion of the method (500) of FIG. 5 where step (504) precedes step (503).

Figure 9:
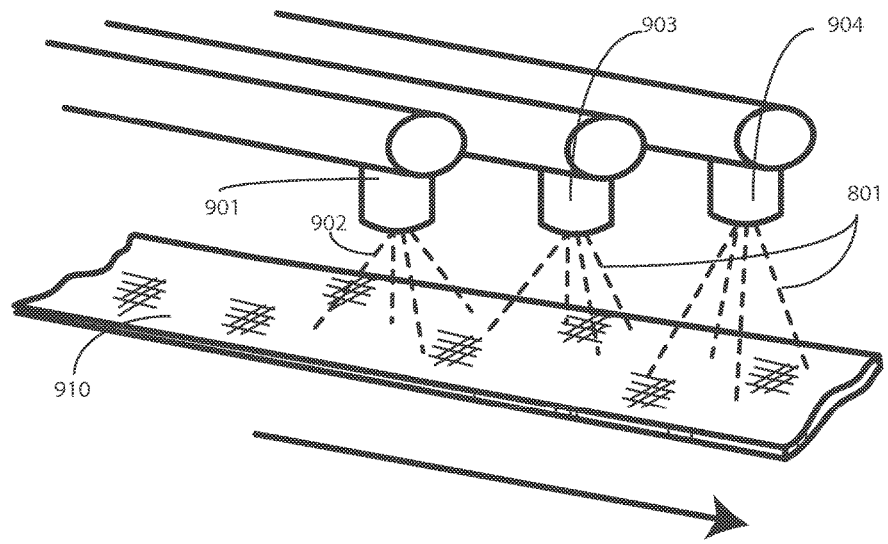
FIG. 9 illustrates an alternate method of forming an alginate dressing comprising carboxymethylcellulose in accordance with one or more embodiments of the invention.

An illustrative operation of a portion of the method (500) of FIG. 5 where step (503) precedes step (504) is shown in FIG. 9. As shown in FIG. 9, a dressing layer 910 has been manufactured from alginate fibers. In one embodiment, the alginate fibers of the dressing layer 910 are wet. They can still be wet from an extrusion bath, or in another embodiment, can be pre-moistened. For example, a moistening spray head 901 can be used to spray a solution 902 along the dressing layer 910. The solution 902 may be a calcium chloride solution or other solution.

One or more of sprayers 903,904 can then be used to apply the aqueous solution 801 comprising the polysaccharide. In this illustrative embodiment, a sheet of the dressing layer 910 is fed under the sprayers 903,904. The sprayers 903,904 can be operated in a continuous fashion to as to apply the aqueous solution 801 in a continual fashion. Alternatively, the sprayers 903,904 can be operated in an intermittent fashion in accordance with a predefined set of instructions used to selectively apply the aqueous solution 801 to the dressing layer 910. The operation of FIG. 9 works well when the dressing layer 910 is woven.

Figure 10:
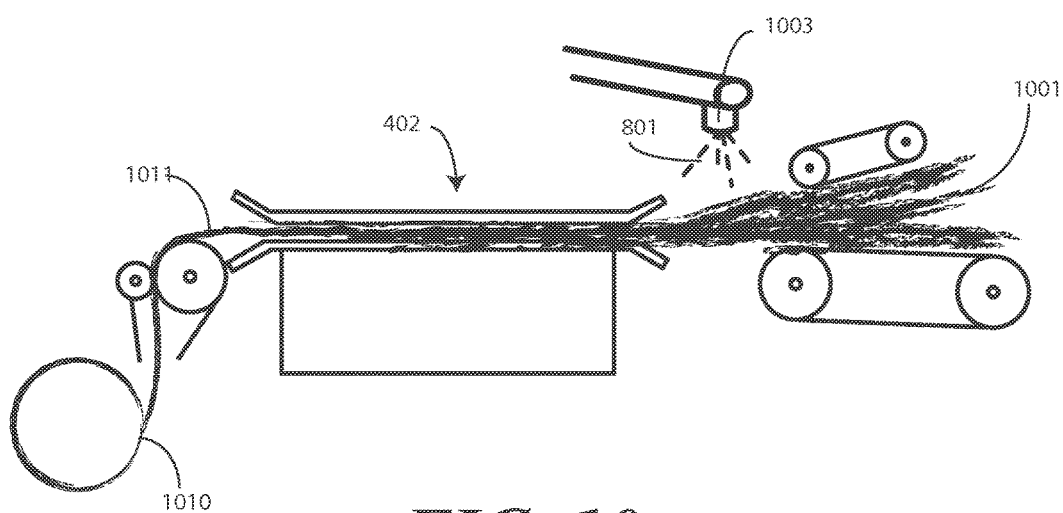
FIG. 10 illustrates yet another alternate method of forming an alginate dressing comprising carboxymethylcellulose in accordance with one or more embodiments of the invention.

Turning now to FIG. 10, illustrated therein is an explanatory operation for applying a polysaccharide to a non-woven layer 1010 for a dressing prior to forming the non-woven layer 1011. As shown in FIG. 10, a non-woven bunch of fibers 1001 are fed into a forming machine 402 where they are interlocked without weaving. In one embodiment, the non-woven bunch of fibers 1001 can still be wet from an extrusion bath. In another embodiment, the non-woven bunch of fibers 1001 can be pre-moistened as they are fed into the forming machine 402.

One or more of sprayers 1003 can then be used to apply the aqueous solution 801 comprising the polysaccharide. The one or more sprayers 1003 can be operated in a continuous fashion to as to apply the aqueous solution 801 in a continual fashion. Alternatively, the one or more sprayers 1003 can be operated in an intermittent fashion in accordance with a predefined set of instructions used to selectively apply the aqueous solution 801 to the non-woven bunch of fibers 1001.

Figure 11:
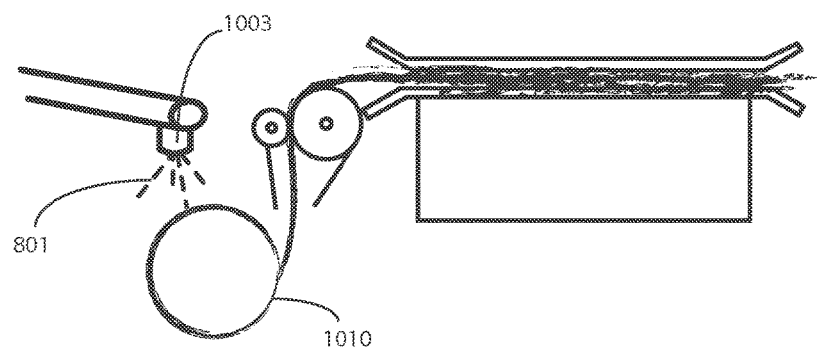
FIG. 11 illustrates yet another alternate method of forming an alginate dressing comprising carboxymethylcellulose in accordance with one or more embodiments of the invention.

Turning to FIG. 11, illustrated therein is substantially the same operation of FIG. 10, however with the placement of the one or more sprayers 1003 moved to a post-interlocking position. As shown in FIG. 11, the non-woven layer 1010 of alginate dressing material is being spooled for later processing. While the spooling process occurs, the one or more sprayers 1003 apply the aqueous solution 801 comprising the polysaccharide. The one or more sprayers 1003 can be operated in a continuous fashion to as to apply the aqueous solution 801 in a continual fashion. Alternatively, the one or more sprayers 1003 can be operated in an intermittent fashion in accordance with a predefined set of instructions used to selectively apply the aqueous solution 801 to the non-woven layer 1010. The embodiment of FIG. 11 offers increased control of any selective deposition process of the aqueous solution 801 due to the fact that the non-woven layer 1010 has completely been formed. As previously described, in one embodiment the non-woven layer 1010 can be wet, such as with liquid from an extrusion bath. In other embodiments, the non-woven layer 1010 can be moistened prior to the one or more sprayers 1003 depositing the aqueous solution 801.

Figure 12:
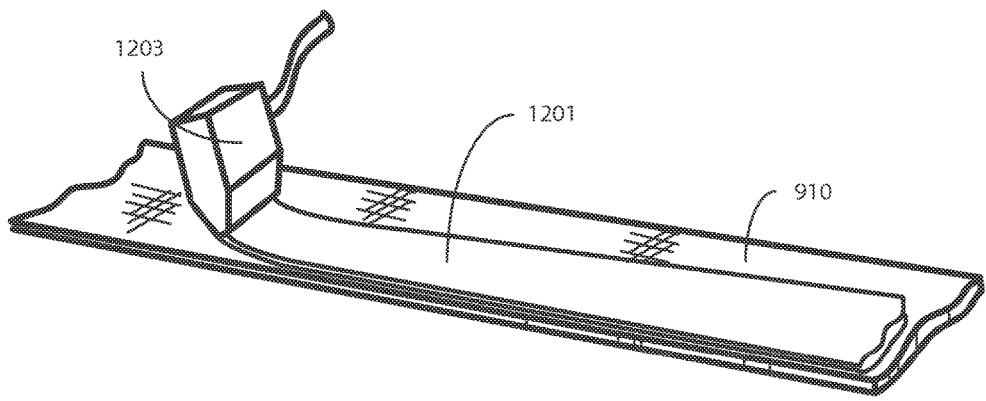
FIG. 12 illustrates yet another alternate method of forming an alginate dressing comprising carboxymethylcellulose in accordance with one or more embodiments of the invention.

Turning to FIG. 12, illustrated therein is an alternate method of applying an aqueous solution 1201 comprising polysaccharide to a dressing layer 910. As shown in FIG. 12, the dressing layer 910 can be fed in sheet form under an applicator 1203 that deposits the aqueous solution 1201 on the dressing layer 910 at a predetermined concentration. In one embodiment, a sufficient amount of aqueous solution 1201 is applied to provide a predetermined amount of the polysaccharide per unit area, or alternatively per unit weight, of the dressing layer 910. The percentage of surface area covered with the aqueous solution 1201, or the percentage by weight, can be selected based upon a particular medical application or desired wound-healing effect. It will be obvious to those of ordinary skill in the art having the benefit of this disclosure that the amount of aqueous solution 1201 applied will vary with application. The application of the aqueous solution 1201, as well as the application of other components such as the medicines or other materials described at step (506) of FIG. 5, step can occur at predetermined temperature, pressure, or acidity. In FIG. 12, the applicator 1203 applies the aqueous solution 1201 continually.

Figure 13:
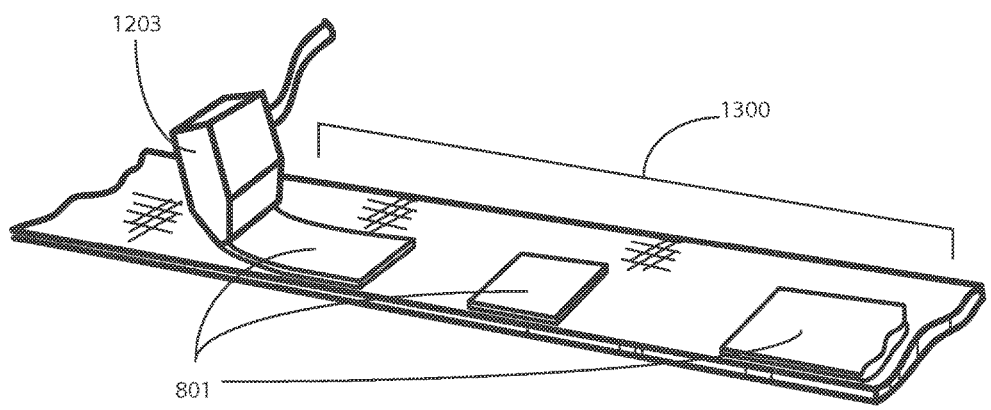
FIG. 13 illustrates yet another alternate method of forming an alginate dressing comprising carboxymethylcellulose in accordance with one or more embodiments of the invention.

Turning to FIG. 13, the applicator 1203 applies the aqueous solution 801 intermittently in a selective pattern 1300. The operation shown in FIG. 13 is similar to that described above with reference to FIG. 9, except that an applicator 1203 is used instead of one or more sprayers (903,904).

Figure 14:
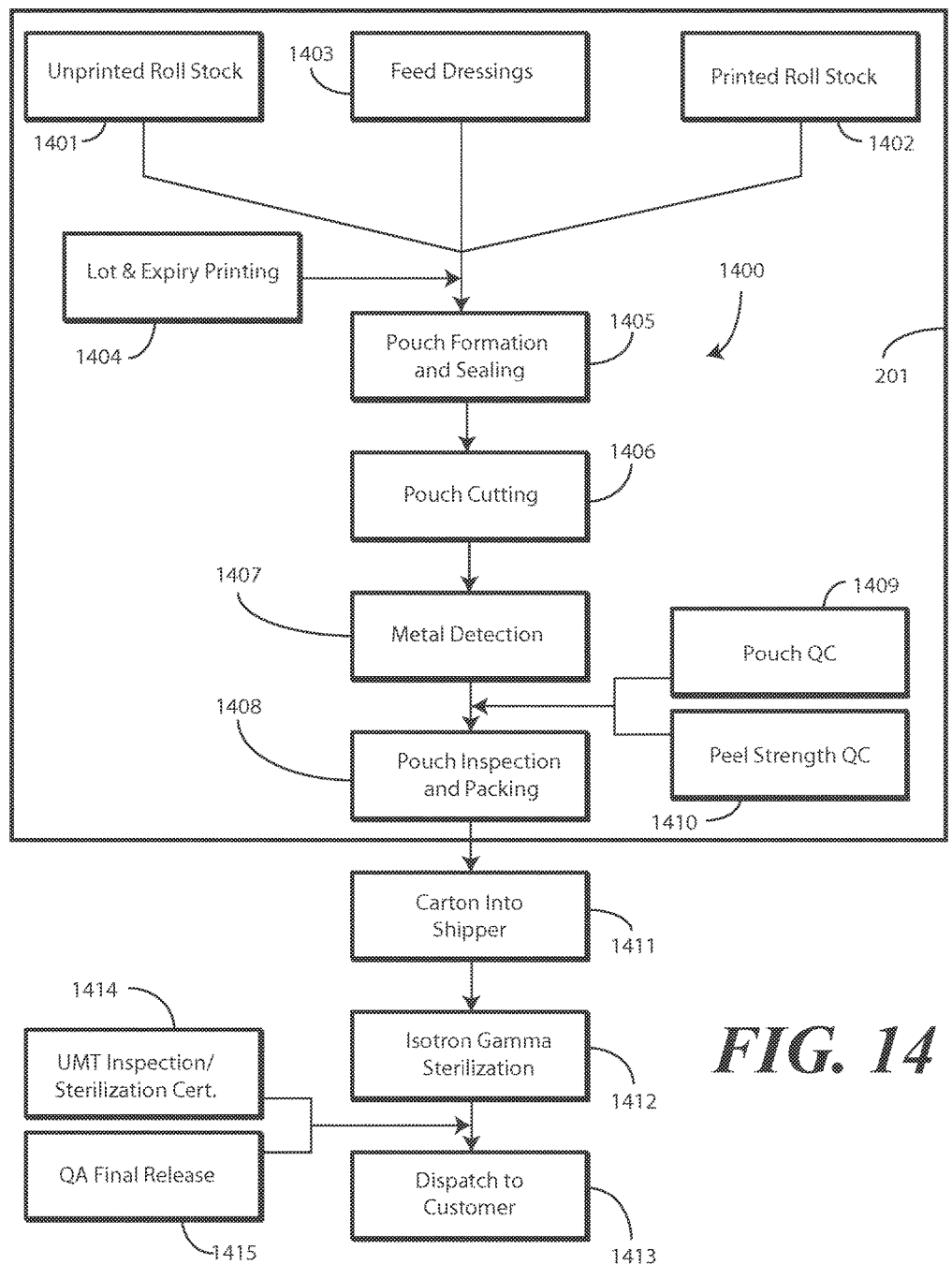
FIG. 14 illustrates a method of making pouches from alginate materials comprising carboxymethylcellulose in accordance with one or more embodiments of the invention.

To this point, the discussion has focused on the manufacture of fibers or dressings. However, embodiments of the present invention also contemplate that other objects of manufacture can be constructed of alginate fibers having deposited carboxymethylcellulose as well. For example, the method 1400 of FIG. 14 illustrates a method of manufacturing pouches in accordance with one or more embodiments of the invention. Pouches are illustrative only, as other objects constructed using the alginate fibers comprising carboxymethylcellulose will be obvious to those of ordinary skill in the art having the benefit of this disclosure.

The raw materials for the method 1400 can be any of unprinted roll stock 1401, feed dressings 1403, or printed roll stock 1402. These raw materials can be optionally printed with lot and expiration information at step 1404. Pouches can then be formed at step 1405 and cut at step 1406, with the formation and cutting occurring in a clean room 201 in one or more embodiments.

In optional step 1407, the resulting pouches can be screened for metal. Metal particulate can be deposited in the pouches during the cutting step. Where this occurs, step 1407 ensures that the metal is removed prior to shipment. The pouches can then be inspected and packed at step 1408. Prior to this step 1408, optional quality control checks for pouch construction at step 1409 and peel strength quality at step 1410 can occur.

Once the packaged pouches exit the clean room 201, they can be put into carton shippers at step 1411. An optional sterilization, such as by gamma irradiation, can occur at step 1412. Final inspection can occur at step 1414. In one embodiment, step 1414 includes a sterilization inspection and results in sterilization certification of the packaged pouches. Final quality assurance inspections can be conducted at step 1415. The resulting product can be dispatched to a customer at step 1413.

Figure 15:
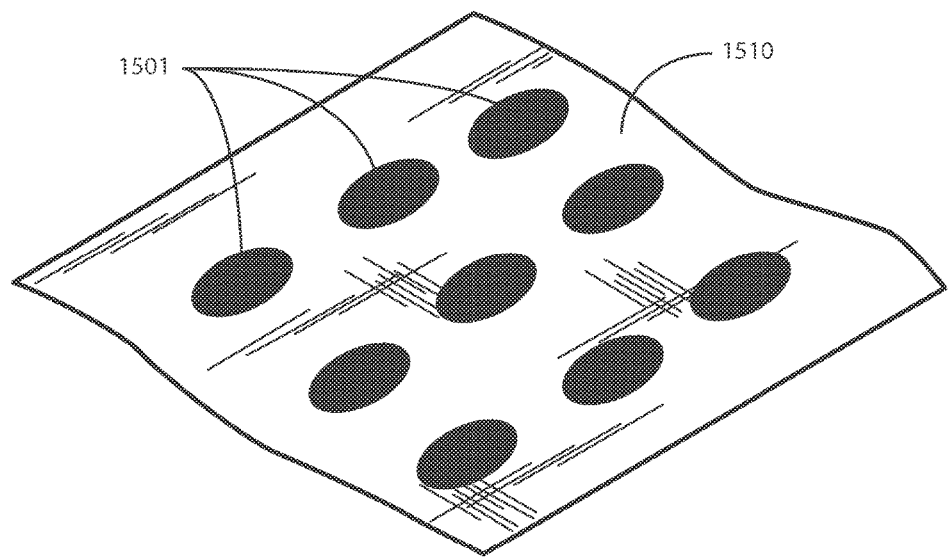
FIGS. 15-18 illustrate various explanatory embodiments of alginate dressings configured in accordance with one or more embodiments of the invention and having selectively deposited carboxymethylcellulose disposed thereon.

As noted above, the fibers, dressings, and pouches of embodiments of the invention have, in some embodiments, carboxymethylcellulose deposited thereon in selective patterns. Examples of some illustrative selective patterns are shown in FIGS. 15-18. Turning first to FIG. 15, illustrated therein is a dressing layer 1510 manufactured from alginate fibers. A polysaccharide 1501, which in this case is carboxymethylcellulose, has been selectively deposited along the dressing layer 1510 in a repeating pattern that is shown as a dotted pattern. The dotted patter is but one of the infinite number of patterns that may be used with embodiments of the invention. Further, other patterns, including linear patterns, polygonal patterns, and curvilinear patterns, will be readily apparent to those of ordinary skill in the art having the benefit of this disclosure.

Figure 16:
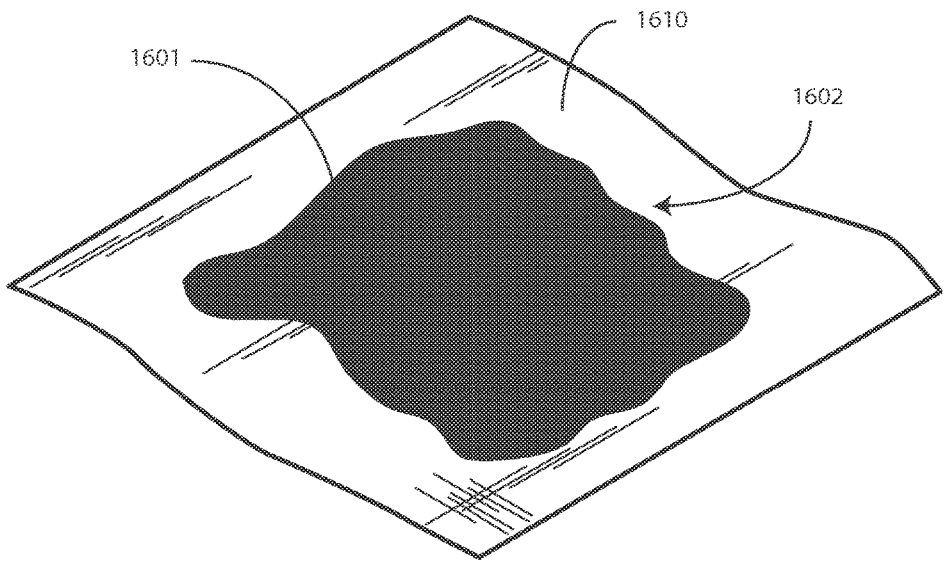

FIG. 16 illustrates a dressing layer 1610 that has deposited thereon carboxymethylcellulose 1601 in a freeform pattern 1602 that covers a predefined wound-covering portion of the dressing layer 1610. The wound-covering portion will vary from application to application. However, to illustrate by example, if the dressing layer 1610 is to be used in a dressing for suture wounds, the wound-covering portion may be linear. By contrast, where the dressing layer 1610 is to be used in a dressing designed for blunt trauma puncture wounds, the would covering portion may be larger along the length and width dimensions as shown in FIG. 16.

Figure 17:
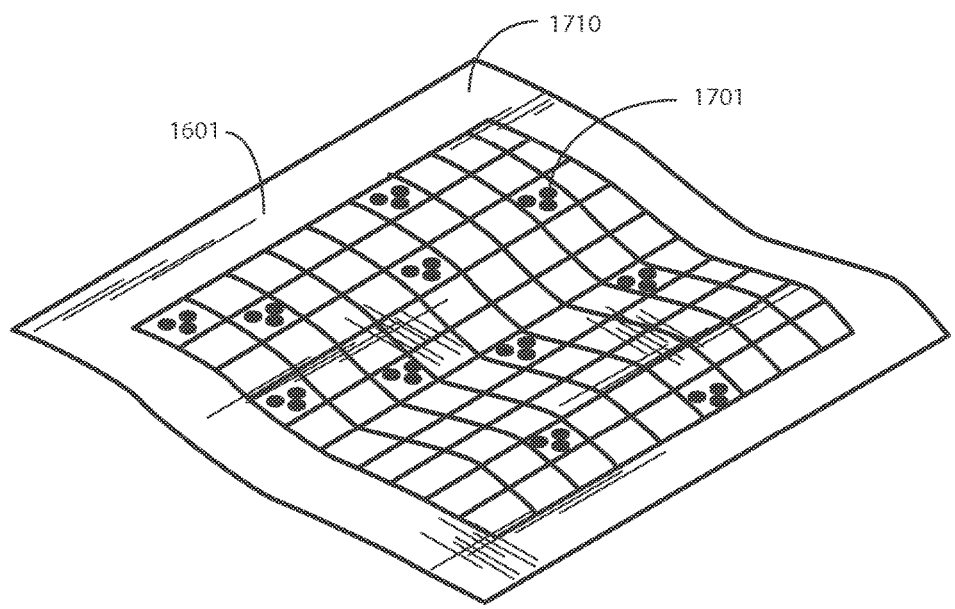

FIG. 17 illustrates a dressing layer 1710 that includes carboxymethylcellulose 1601 that has been selectively deposited. As shown in FIG. 17, the dressing layer also includes a doped medicinal agent 1701, which in this case comprises silver ions. As shown, the carboxymethylcellulose 1601 has been selectively deposited about the silver ions such that the two do not overlap. In other embodiments, the carboxymethylcellulose 1601 will be deposited such that portions of the carboxymethylcellulose 1601 overlap the silver ions, but with some portions of the silver ions not overlapping the carboxymethylcellulose 1601.

Figure 18:
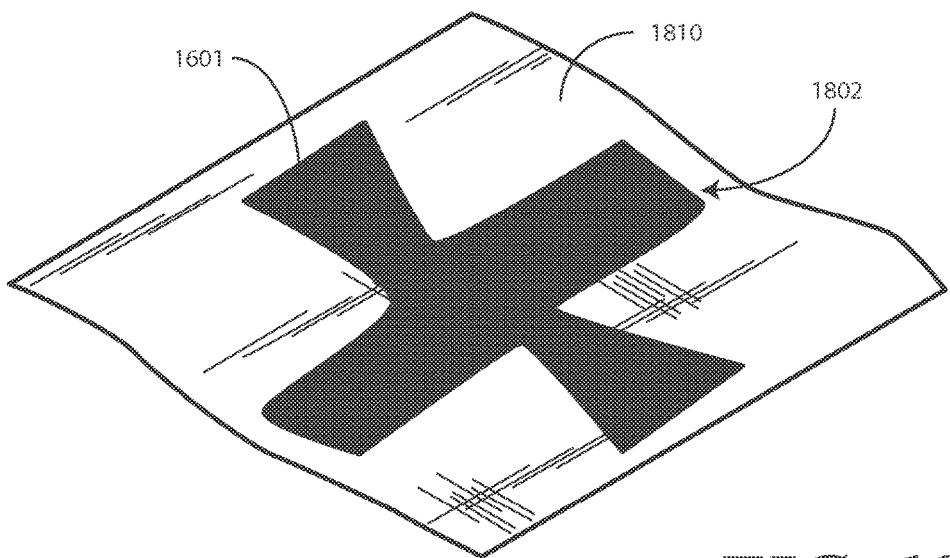

FIG. 18 illustrates a dressing layer 1810 having carboxymethylcellulose 1601 deposited thereon in a wound-specific pattern 1802. The wound-specific pattern 1802 of FIG. 18 imitates a form of "butterfly" that may be suitable for a multi-dimensional incision used during a surgical operation. Other wound-specific patterns 1802 will be obvious to those of ordinary skill in the art having the benefit of this disclosure.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A wound dressing, comprising:
a dressing layer manufactured from alginate fibers; and carboxymethylcellulose;
the carboxymethylcellulose is selectively deposited along the dressing layer with a spray of an aqueous solution.

2. The wound dressing of claim 1, wherein the dressing layer comprises silver ions.

3. The wound dressing of claim 1, wherein the carboxymethylcellulose is deposited in a repeating pattern along the dressing layer.

4. The wound dressing of claim 1, wherein the carboxymethylcellulose is deposited only on a wound-covering sub-portion of the dressing layer.

5. The wound dressing of claim 1, wherein the dressing layer is non-woven.

6. The wound dressing of claim 1, the alginate fibers comprising extruded alginate fibers.

7. The wound dressing of claim 1, wherein the carboxymethylcellulose is about fifteen percent by weight of the one or more alginate fibers.

8. The wound dressing of claim 1, further comprising a medication.

9. The wound dressing of claim 1, the alginate fibers flash dried.

10. The wound dressing of claim 1, the carboxymethylcellulose selectively deposited along the dressing layer with the spray of the aqueous solution while the alginate fibers are wet.

11. The wound dressing of claim 1, the spray comprising a carboxymethylcellulose concentration of about ten percent.

12. The wound dressing of claim 1, the spray applied to only selected portions of the wound dressing.

13. The wound dressing of claim 12, the selected portions comprising wound covering portions of the wound dressing.

* * * * *